US012630620B2

(12) United States Patent
Zhang et al.

(10) Patent No.: US 12,630,620 B2
(45) Date of Patent: May 19, 2026

(54) ANTI-GDF15 NEUTRALIZING MONOCLONAL ANTIBODY AND USE THEREOF

(71) Applicant: NuAge (Shaanxi) Medical and Technology Company Ltd, Xi'an (CN)

(72) Inventors: Yingqi Zhang, Xi'an (CN); Meng Li, Xi'an (CN); Chuanyang Xu, Xi'an (CN); Zhaowei Wang, Xi'an (CN); Weina Li, Xi'an (CN); Lei He, Xi'an (CN); Cun Zhang, Xi'an (CN); Qiang Hao, Xi'an (CN); Ning Zhao, Xi'an (CN)

(73) Assignee: NuAge (Shaanxi) Medical and Technology Company Ltd, Xi'an (CN)

( * ) Notice: Subject to any disclaimer, the term of this patent is extended or adjusted under 35 U.S.C. 154(b) by 739 days.

(21) Appl. No.: 17/958,259

(22) Filed: Sep. 30, 2022

(65) Prior Publication Data

US 2023/0203145 A1     Jun. 29, 2023

Related U.S. Application Data

(63) Continuation of application No. PCT/CN2021/082814, filed on Mar. 24, 2021.

(30) Foreign Application Priority Data

Mar. 30, 2020     (CN) .......................... 202010238389.9

(51) Int. Cl.
*C07K 16/22*          (2006.01)
*A61P 35/00*          (2006.01)

(52) U.S. Cl.
CPC .............. *C07K 16/22* (2013.01); *A61P 35/00* (2018.01); *C07K 2317/565* (2013.01)

(58) Field of Classification Search
CPC .............. C07K 16/22; C07K 2317/565; C07K 2317/73; C07K 2317/76; C07K 2317/92; C07K 2317/56; A61P 35/00; A61P 1/14; A61P 3/00; A61P 3/04; A61K 2039/505
See application file for complete search history.

(56) References Cited

U.S. PATENT DOCUMENTS

2015/0239968 A1*   8/2015  Wischhusen ........... A61K 45/06
435/320.1

FOREIGN PATENT DOCUMENTS

| CN | 101852804 A | 10/2010 |
| CN | 105073133 A | 11/2015 |
| CN | 108137689 A | 6/2018 |
| CN | 109071647 A | 12/2018 |
| CN | 111393526 A | 7/2020 |
| WO | 2017189724 A1 | 11/2017 |

OTHER PUBLICATIONS

Emerson et al. (Frontiers in Physiology, 9: 1-7, 2018).*
International Search Report (PCT /CN2021/082814); Date of Mailing: Jun. 25, 2021.
CN First Office Action(202010238389.9); Date of Mailing: Aug. 5, 2021.
C-Fos-separation-from-Lamin-A_C-by-GDF15-promotes-colon-cancer-invasion-and-metastasis-in-inflammatory-microenvironment, Jun. 2019 Nem II Jun. 4, 2025.
Breakdown-of-B-Cell-Tolerance-in-a-Mouse-Model-of-Systemic-Lupus-Erythematosus, Mar. 1995 NBM II Jun. 4, 2025.
Growth-differentiation-factor-15-contributes-to-marrow-adipocyte-remodeling-in-response-to-the-growth-of-leukemic-cells, 2018 NBM II Jun. 4, 2025.

* cited by examiner

*Primary Examiner* — Nelson B Moseley, II
(74) *Attorney, Agent, or Firm* — Wiersch Law Group

(57)          ABSTRACT

The present application discloses two anti-GDF15 neutralizing monoclonal antibodies and uses thereof. The variable regions of the light chain and heavy chain of the antibodies G1 and G2 with neutralizing activity are provided. Anti-GDF15 mouse monoclonal antibodies were prepared by the hybridoma technology, anti-GDF15 hybridoma cell lines capable of stable secretion with high specificity were screened out, ascites were prepared to obtain high-specificity and high-affinity anti-GDF15 monoclonal antibodies and two anti-GDF15 monoclonal antibodies with neutralizing activity were identified for the first time by constructing an antibody neutralization detection system. On the basis of the study of immune regulation of GDF15, the inhibitory effect of the neutralizing monoclonal antibodies on tumor growth is verified by establishing a co-culture system of lymphocytes and tumor cells and the tumor-bearing experiment in mice, which lays a foundation for humanization of antibodies and the use thereof in tumor immunotherapy and metabolism related diseases.

5 Claims, 9 Drawing Sheets

Specification includes a Sequence Listing.

FIG. 1
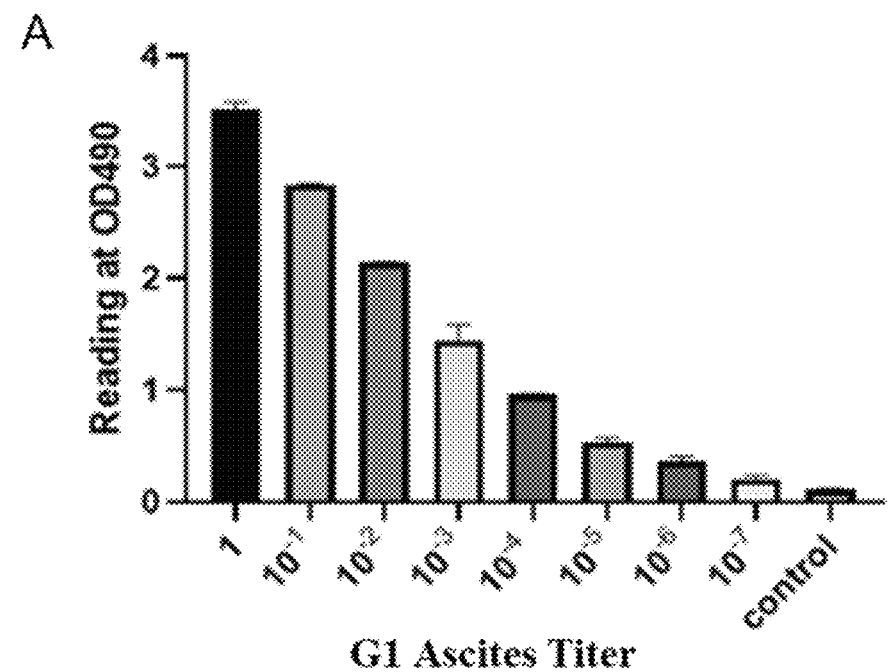
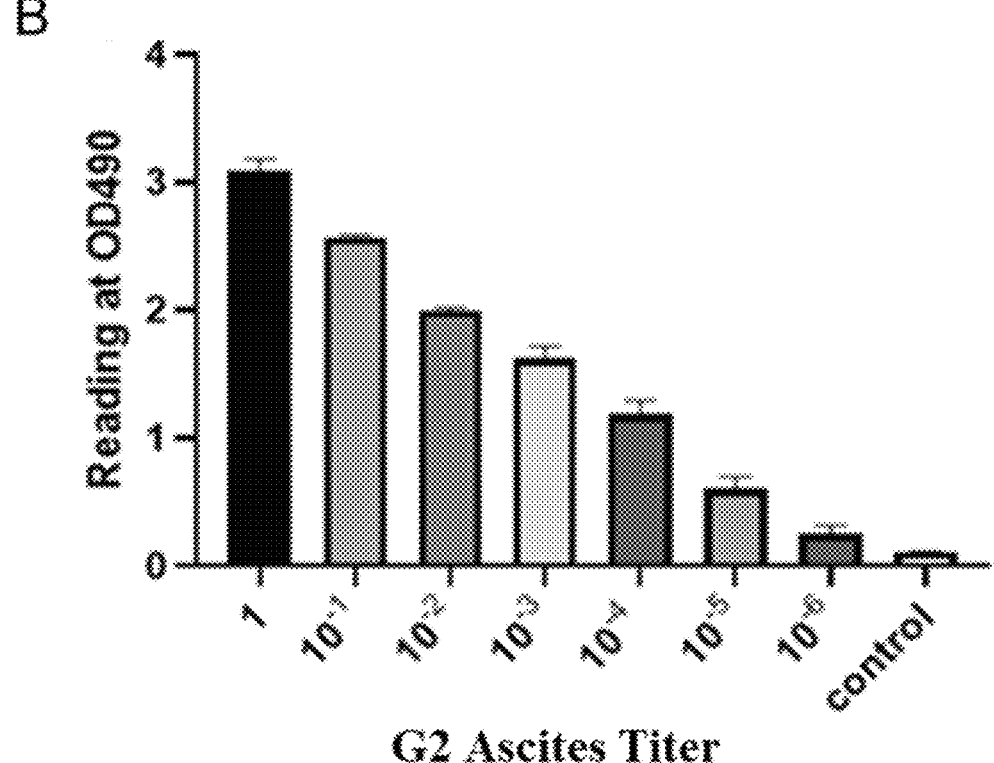

FIG. 3A

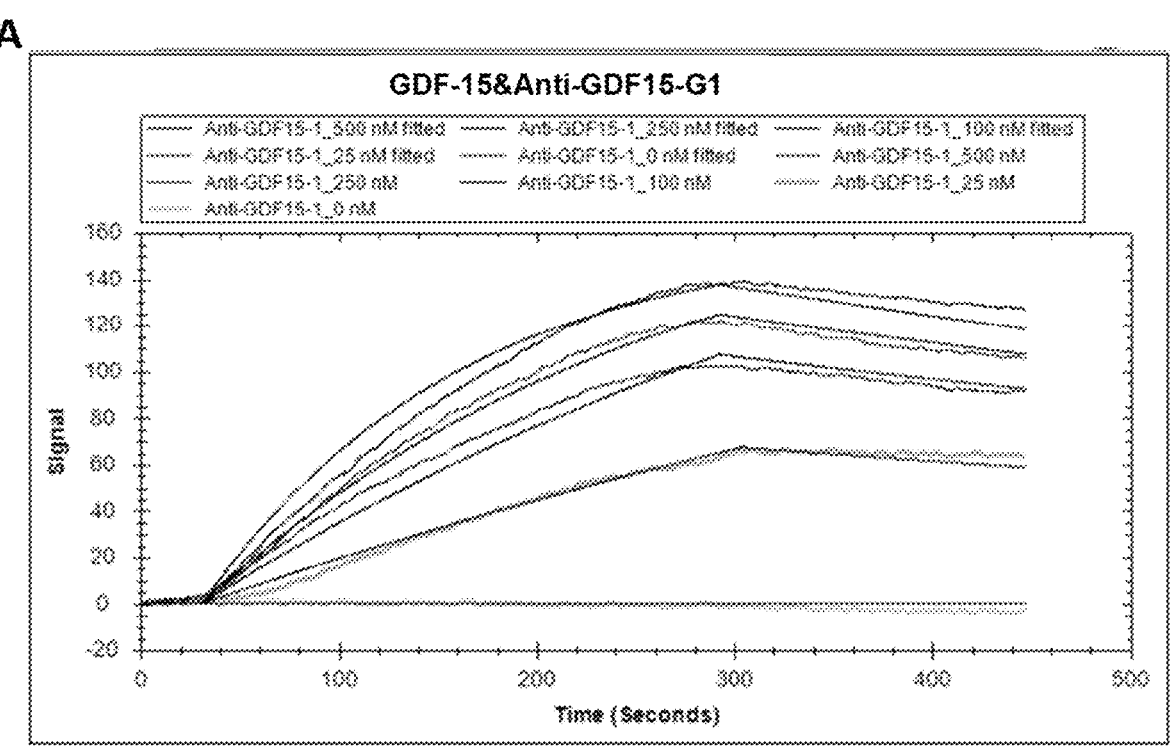

Evaluation type: OneToOne

| Curve name | Bmax (Signal) | ka [1/(M*s)] | kd [1/s] | KD (M) | BI (Signal) |
|---|---|---|---|---|---|
| Anti-GDF15-1_500 nM fitted | 181.10 (±6.41e-2) | 1.36e4 (±3.11e1) | 9.69e-4 (±5.58e-7) | 7.14e-8 (±2.05e-10) | 0.16 (±1.30e-2) |
| Anti-GDF15-1_100 nM fitted | 403.46 (±8.35e-2) | 1.36e4 (±3.11e1) | 9.69e-4 (±5.58e-7) | 7.14e-8 (±2.05e-10) | 0.16 (±1.30e-2) |
| Anti-GDF15-1_0 nM fitted | 137641.52 (±9.91e4) | 1.36e4 (±3.11e1) | 9.69e-4 (±5.58e-7) | 7.14e-8 (±2.05e-10) | 0.16 (±1.30e-2) |
| Anti-GDF15-1_250 nM fitted | 235.65 (±4.12e-2) | 1.36e4 (±3.11e1) | 9.69e-4 (±5.58e-7) | 7.14e-8 (±2.05e-10) | 0.16 (±1.30e-2) |
| Anti-GDF15-1_25 nM fitted | 867.68 (±1.38e-1) | 1.36e4 (±3.11e1) | 9.69e-4 (±5.58e-7) | 7.14e-8 (±2.05e-10) | 0.16 (±1.30e-2) |

| Curve name | Chi2 (Signal^2) | U-value: kd [%] |
|---|---|---|
| Anti-GDF15-1_500 nM fitted | 15.37 | 1.60 |
| Anti-GDF15-1_100 nM fitted | 15.37 | 1.60 |
| Anti-GDF15-1_0 nM fitted | 15.37 | 1.60 |
| Anti-GDF15-1_250 nM fitted | 15.37 | 1.60 |
| Anti-GDF15-1_25 nM fitted | 15.37 | 1.60 |

FIG. 3B

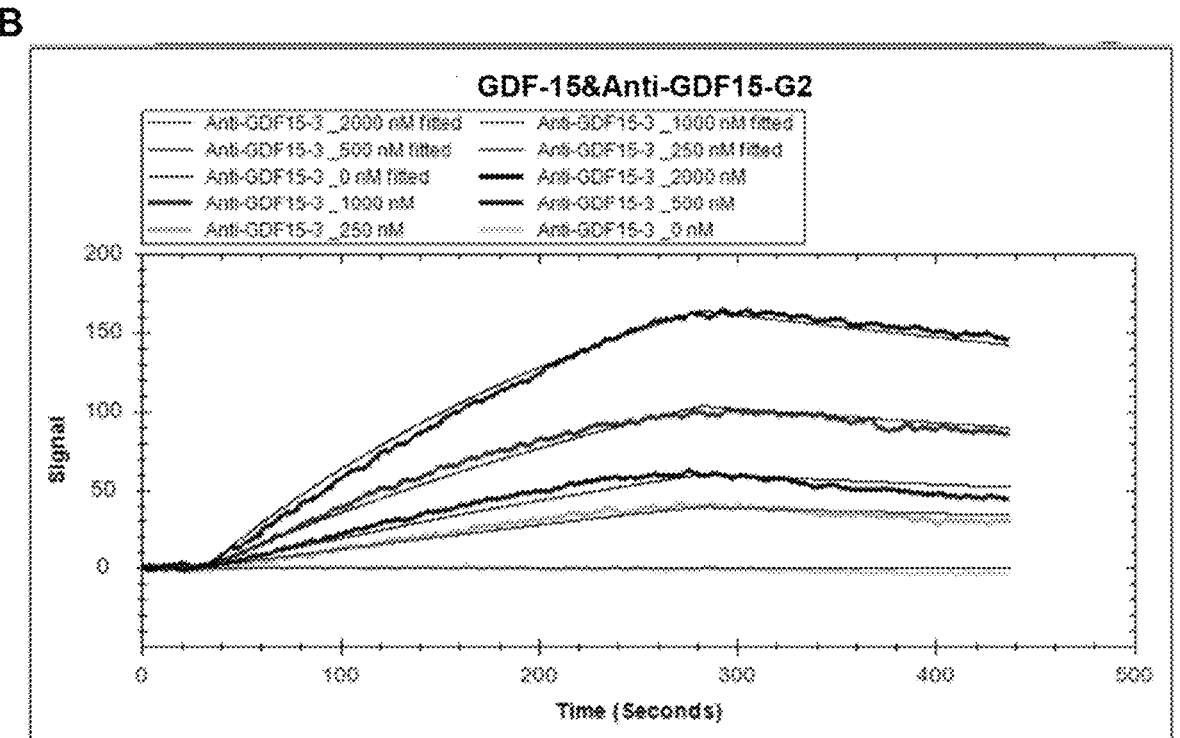

Evaluation type: OneToOne

| Curve name | Bmax (Signal) | ka (1/(M*s)) | kd (1/s) | KD (M) | Rl (Signal) |
|---|---|---|---|---|---|
| Anti-GDF15-3 _0 nM fitted | 72423.87 (±8.22e4) | 1.63e3 (±1.42e1) | 9.34e-4 (±5.82e-6) | 5.72e-7 (±8.03e-9) | 0.19 (±1.81e-3) |
| Anti-GDF15-3 _500 nM fitted | 359.11 (±1.06e0) | 1.63e3 (±1.42e1) | 9.34e-4 (±5.82e-6) | 5.72e-7 (±8.03e-9) | 0.19 (±1.81e-3) |
| Anti-GDF15-3 _1000 nM fitted | 341.25 (±4.91e-2) | 1.63e3 (±1.42e1) | 9.34e-4 (±5.82e-6) | 5.72e-7 (±8.03e-9) | 0.19 (±1.81e-3) |
| Anti-GDF15-3 _250 nM fitted | 444.32 (±9.34e-1) | 1.63e3 (±1.42e1) | 9.34e-4 (±5.82e-6) | 5.72e-7 (±8.03e-9) | 0.19 (±1.81e-3) |
| Anti-GDF15-3 _2000 nM fitted | 333.22 (±2.96e-2) | 1.63e3 (±1.42e1) | 9.34e-4 (±5.82e-6) | 5.72e-7 (±8.03e-9) | 0.19 (±1.81e-3) |

| Curve name | Chi2 (Signal^2) | U-value: Bmax/ka (%) |
|---|---|---|
| Anti-GDF15-3 _0 nM fitted | 11.54 | 4.60 |
| Anti-GDF15-3 _500 nM fitted | 11.54 | 4.60 |
| Anti-GDF15-3 _1000 nM fitted | 11.54 | 4.60 |
| Anti-GDF15-3 _250 nM fitted | 11.54 | 4.60 |
| Anti-GDF15-3 _2000 nM fitted | 11.54 | 4.60 |

FIG. 5
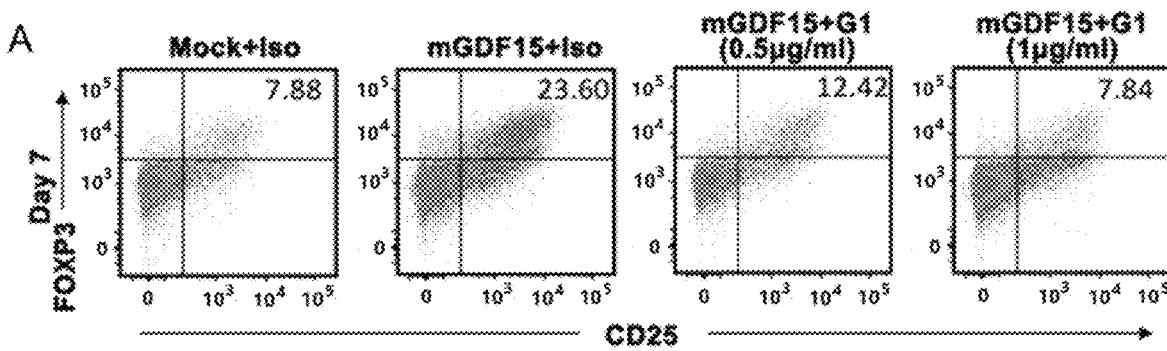
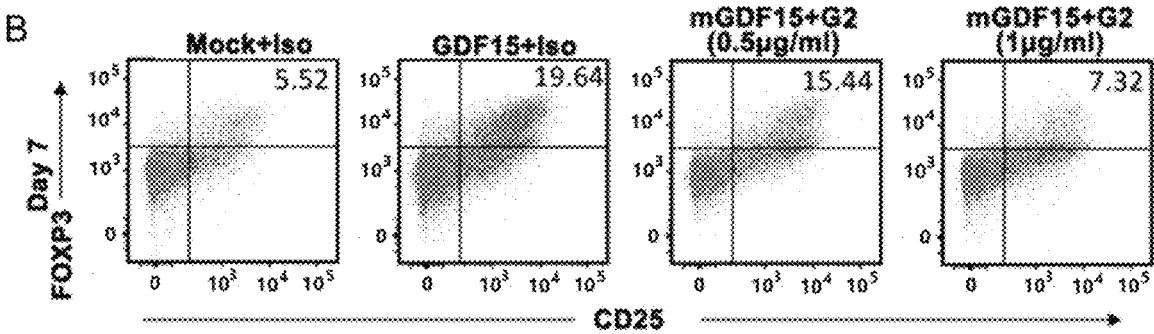
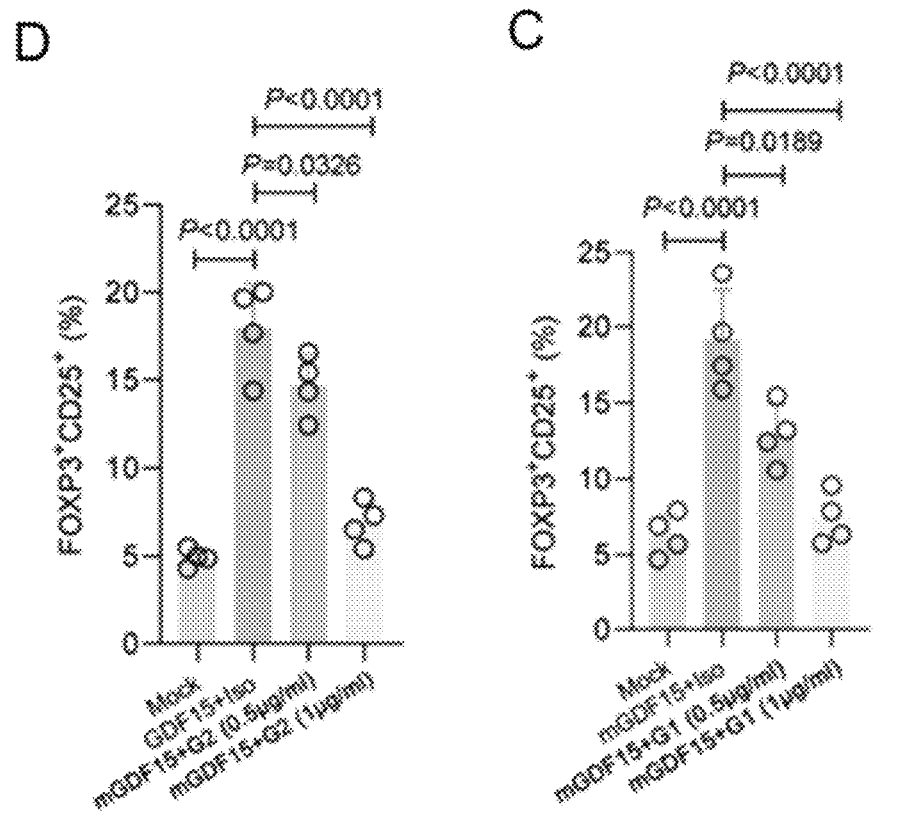

FIG. 6
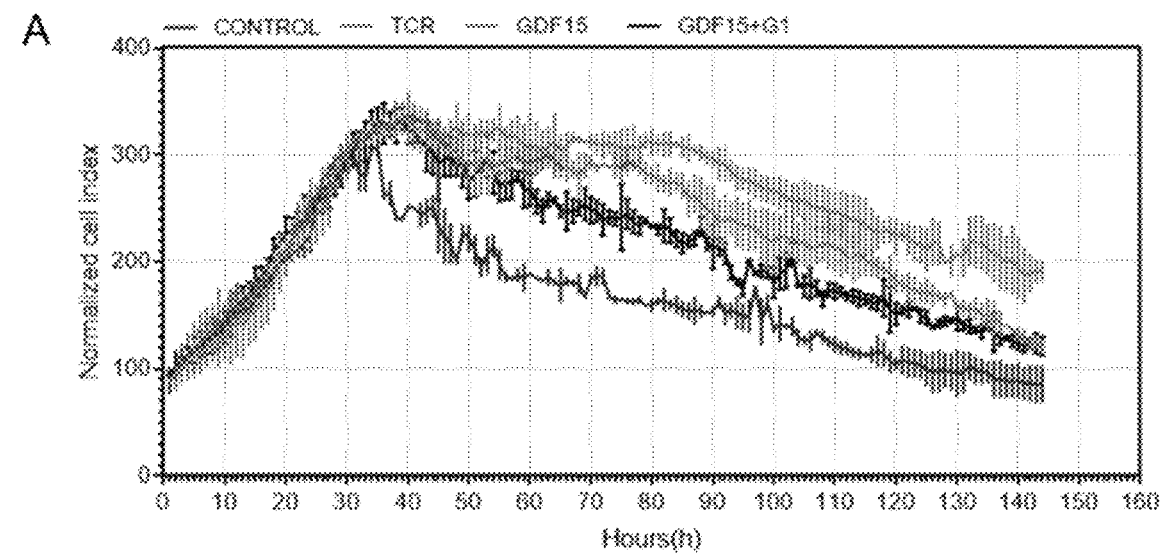
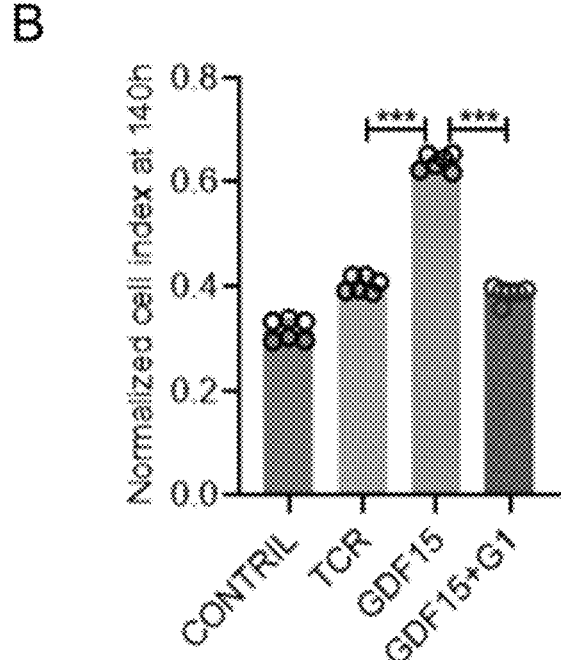

FIG. 7
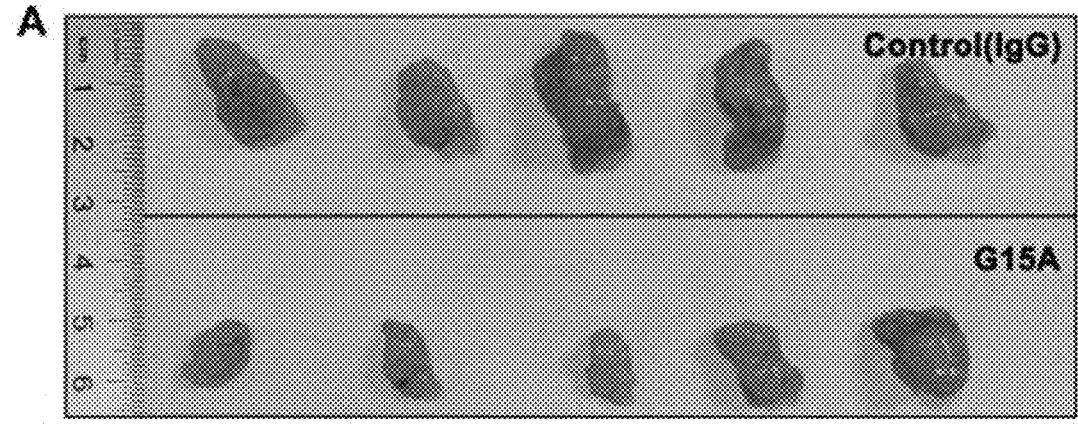
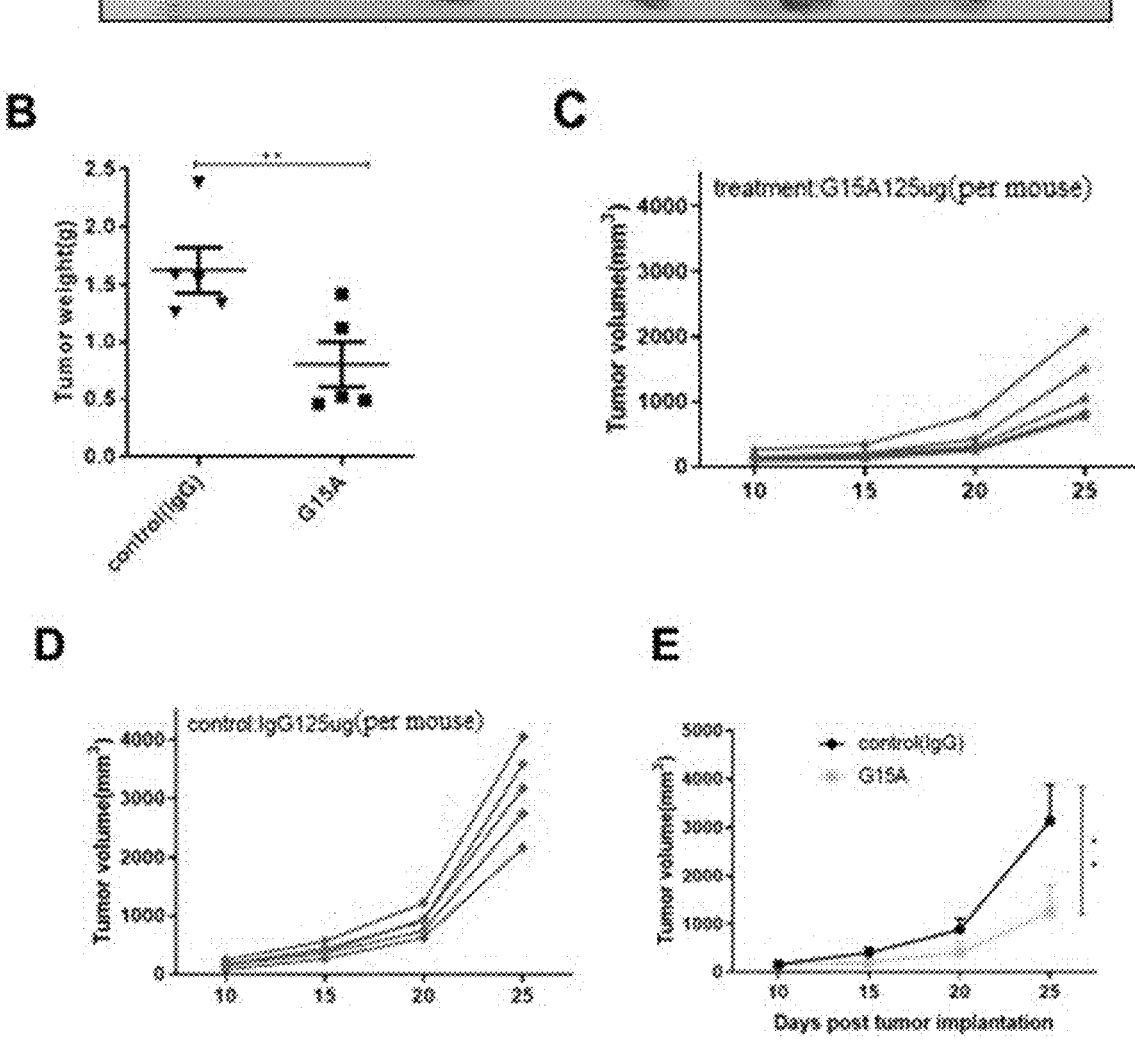

FIG. 8
A  Hepa1-6-Luc Day 28
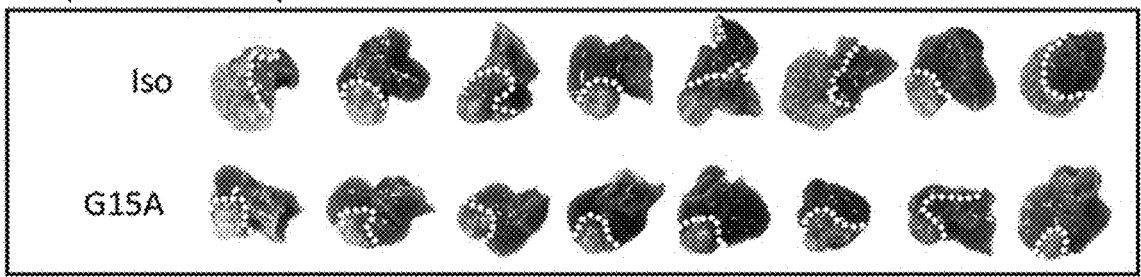
B
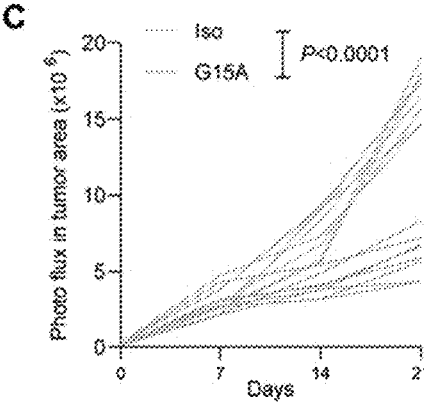
C

ANTI-GDF15 NEUTRALIZING MONOCLONAL ANTIBODY AND USE THEREOF

REFERENCE TO SEQUENCE LISTING

The present application is being filed along with a Sequence Listing in electronic format. The Sequence Listing is provided as a file entitled DF223393US-SEQUENCE LISTING ST.26, created Sep. 30, 2022, which is approximately 9.34 Kb in size. The information in the electronic format of the Sequence Listing is incorporated herein by reference in its entirety.

TECHNICAL FIELD

The present application belongs to the technical field of biomedical technology and relates to monoclonal antibodies, in particular to two anti-GDF15 neutralizing monoclonal antibodies and uses thereof.

BACKGROUND

Growth differentiation factor 15 (GDF15) is one of the distal members of the Transforming growth factor β(TGF-β) superfamily, also known as Macrophage Inhibitory Factor-1 (MIC-1), Placental Bone Morphogenetic Protein (PLAB), Placental Transforming Growth Factor β(PTGFβ), Non-steroidal Anti-Inflammatory Drug Activation Gene-1 (NAG-1), Prostate Derived Long Factor (PDF), and the like. GDF15 levels are low under normal physiological conditions, while GDF15 levels are significantly elevated in the development of cardiovascular, tumor and inflammation-related diseases and are closely associated with poor prognosis of the disease.

1. Molecular Characteristics of GDF15

GDF15 is one of the distal members of the TGF-β superfamily, whose gene contains two exons and one intron and is highly conserved among species. The GDF15 molecule includes a signal peptide, a propeptide region, and a mature region at the carboxy terminus. Differentiated from other superfamily members, GDF15 is a unique intrachain carboxy-terminal cysteine domain. The GDF15 precursor polypeptide forms stable homodimers through interchain disulfide bonds at the carboxy terminus, with the mature 25 kDa homodimer produced and secreted after hydrolytic removal of the amino-terminal propeptide. The mature protein it encodes has a cysteine knot composed of seven conserved carboxy-terminal cysteine residues. The GDF15 promoter has a number of regulatory sites for transcription factors, such as HIF1α, p53, EGR-1 and Sp1, among others. GDF15 is also a downstream key target gene of p53, EGR-1 and AKT/GSK-3β pathways.

2. Role of GDF15 in Appetite Regulation, Obesity and Metabolism

Numerous clinical studies have shown that GDF15 is associated with diseases related with obesity, insulin resistance, anorexia and weight loss due to metabolic disorders. Its high expression is closely associated with anorexia during pregnancy, anorexia initiated by inflammatory responses, and dyscrasias (anorexia, wasting) in patients with advanced tumors. GDF15 transgenic mice exhibited wasting and decreased appetite compared to normal mice, and injection of exogenous GDF15 also suppressed appetite body weight in mice. In August 2017, four pharmaceutical companies Novo Nordisk, Janssen, Eli Lilly and Merck simultaneously reported that the receptor for GDF15 was a Glial-cell-derived neurotrophic factors family receptor a-like (GFRAL), and deletion of this receptor completely inhibited the appetite suppression and weight regulation functions of GDF15. GDF15 has become one of the research hotspots in terms of weight regulation and metabolic regulation, and its value as a drug development for weight control is worth further attention.

3. GDF15 and Inflammatory Responses and Immune Modulation in Tumor Microenvironment GDF15 is significantly up-regulated in many inflammation-related diseases such as acute infections, tumors, cardiovascular diseases. However, the role of GDF15 on the development of inflammation and the effect on immune cells are not well reported and further studies are still to be developed in combination with the relevant environmental factors for chronic and acute inflammatory responses. There is less research on GDF15 in terms of immunomodulation and research is currently focused primarily on macrophages. GDF15 is closely related to the biological function of macrophages, being able to regulate the typing of macrophages by upregulating their oxidative function, resulting in M2-type polarization of macrophages. M2-type macrophages play a suppressive role in anti-tumor immunity, and are able to promote immune escape of tumor cells by secreting large amounts of immunosuppressive cytokines. On investigation of other immunomodulatory effects of GDF15, the applicant's group previously identified GDF15 as a key molecule for liver cancer induction of Regulatory T cells (Tregs) generation, demonstrating that GDF15 is able to induce Tregs generation and up-regulate the suppressive function of Tregs, while also illustrating the effect of GDF15 on macrophage, NK cell and DC function.

Thus, these studies demonstrate that GDF15, a molecule that exerts inhibitory effects on a variety of immune cells, can serve as a potential target for tumor immunotherapy, and its blockade would be effective in enhancing anti-tumor immune responses.

SUMMARY

It is an object of the present application to provide anti-GDF15 neutralizing monoclonal antibodies and uses thereof.

In order to achieve the above objects, the present application is achieved with the following technical solutions.

The present application discloses an anti-GDF15 neutralizing monoclonal antibody G1, including a light chain and a heavy chain, wherein, three complementarity determining region sequences of a variable region of the light chain are respectively:

```
CDR1:
Arg-Ala-Ser-Glu-Asn-Ile-Tyr-Ser-Asn-Leu-Ala;

CDR2:
Val-Ala-Thr-Asn-Leu-Val-Asp;

CDR3:
Gln-His-Phe-Trp-Gly-Thr-Pro-Trp-Thr;
``` three complementarity determining region sequences of a variable region of the heavy chain are respectively:

```
CDR1:
Ser-Ala-Tyr-Ala-Trp-Asn;

CDR2:
Tyr-Ile-Ser-Tyr-Ser-Gly-Ser-Thr-Ser-Tyr-Asn-Pro-
Ser-Leu-Lys-Ser;

CDR3:
Gly-Gly-Asp-Ala-Glu-Asp-Tyr.
```

Preferably, the amino acid sequence of the variable region of the light chain is as shown in SEQ.ID.NO. 1 and the amino acid sequence of the variable region of the heavy chain is as shown in SEQ.ID.NO. 2.

Preferably, the nucleotide sequence encoding the variable region of the light chain is as shown in SEQ.ID.NO.5 and the nucleotide sequence encoding the variable region of the heavy chain is as shown in SEQ.ID.NO.6.

The present application further discloses an anti-GDF15 neutralizing monoclonal antibody G2 including a light chain and a heavy chain, wherein, three complementarity determining region sequences of a variable region of the light chain are respectively:

```
CDR1:
Arg-Ala-Ser-Ser-Ser-Val-Ser-Tyr-Met-His;

CDR2:
Ala-Thr-Ser-Asn-Leu-Ala-Ser;

CDR3:
Gln-Gln-Trp-Ser-Ser-Asn-Pro-Pro-Phe-Thr;
``` three complementarity determining region sequences of a variable region of the heavy chain are respectively:

```
CDR1:
Asp-Tyr-Tyr-Ile-Asn;

CDR2:
Glu-Ile-Tyr-Pro-Gly-Ser-Gly-Asn-Thr-Tyr-Tyr-Asn-
Glu-Lys-Phe-Lys-Gly;

CDR3:
Val-Arg-Ala-Leu-Leu-Arg-Pro-Leu-Ala-Met-Asp-Tyr.
```

Preferably, the amino acid sequence of the variable region of the light chain of the monoclonal antibody G2 is as shown in SEQ.ID.NO.3 and the amino acid sequence of the variable region of the heavy chain is as shown in SEQ.ID.NO.4.

Preferably, the nucleotide sequence encoding the variable region of the light chain is as shown in SEQ.ID.NO.7 and the nucleotide sequence encoding the variable region of the heavy chain is as shown in SEQ.ID.NO.8.

The present application further discloses use of the above anti-GDF15 neutralizing monoclonal antibody G1 or the above anti-GDF15 neutralizing monoclonal antibody G2 in the manufacture of an anti-tumor medicament or a tumor immunotherapy medicament.

The present application further discloses use of the above anti-GDF15 neutralizing monoclonal antibody G1 or the above anti-GDF15 neutralizing monoclonal antibody G2 in the manufacture of a medicament associated with a metabolic disease.

Preferably, the metabolic disease comprises obesity, anorexia or cachexia.

The present application further discloses use of the above anti-GDF15 neutralizing monoclonal antibody G1 or the above anti-GDF15 neutralizing monoclonal antibody G2 in an immunologic test assay for non-disease theranostic purposes.

Compared to the prior art, the present application has the following beneficial effects:

1. The anti-GDF15 neutralizing monoclonal antibodies G1 and G2 provided herein are two anti-GDF15 neutralizing monoclonal antibodies with high affinity and high specificity. They can be used in studies such as immunotherapy of tumors and energy regulation in the body, which provides new approaches and strategies for immunotherapy of tumors and metabolism related diseases such as obesity, anorexia and cachexia.

2. The present application provides genes and amino acid sequences of the variable regions of the light chains and heavy chains of the anti-GDF15 neutralizing monoclonal antibodies G1 and G2.

3. The CDR regions of the variable regions of the light and heavy chains are analyzed, based on which support is provided for the construction of highly specific, high-affinity anti-GDF15 chimeric or humanized genetically engineered antibodies.

BRIEF DESCRIPTION OF DRAWINGS

FIG. 1 shows the ascites titer assay results of the anti-GDF15 monoclonal antibodies; wherein A is the ascites titer result prepared from the hybridoma corresponding to the antibody G1; B is the ascites titer result prepared from the hybridoma corresponding to the antibody G2;

FIG. 3A and FIG. 3B show the affinity assay result of an anti-GDF15 monoclonal antibody G15A to the GDF15 recombinant protein as determined by SPR; wherein A is the affinity binding curve of respective concentration gradients and affinity parameters of the antibody G1; B is the affinity binding curve of respective concentration gradients and affinity parameters of the antibody G2;

FIG. 5 shows the results of the neutralizing activity of the anti-GDF15 monoclonal antibodies G1 and G2 as determined by a flow cytometry experiment;

Figure 2:
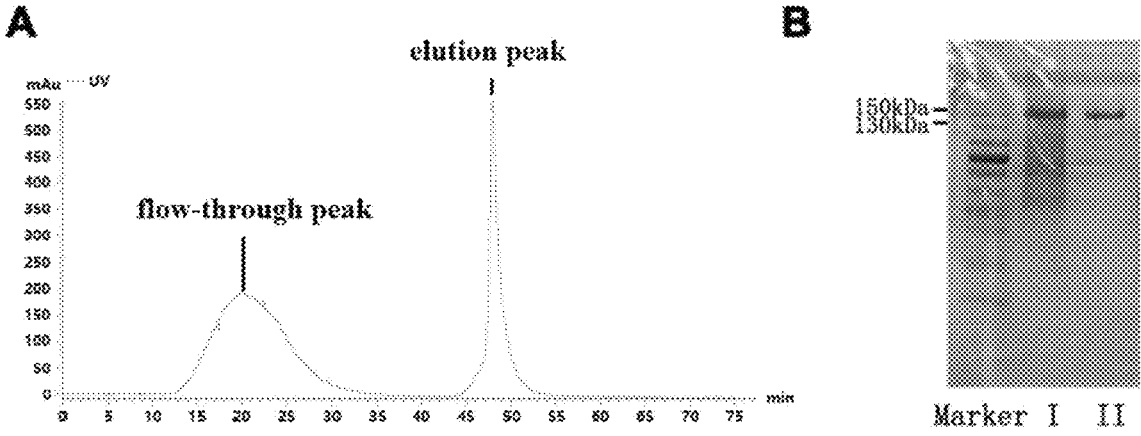
FIG. 2 shows the purification result of the anti-GDF15 monoclonal antibodies; wherein A is the affinity chromatography result of an AKTA FPLC chromatography purification system, with the first peak being the unbound sample loaded and the second peak being the sample after PH2.7 glycine elution; B is a SDS-PAGE profile, I is a sample before affinity chromatography, and II is a sample after affinity chromatography.

wherein A and B are the results of the proportion of Treg cells (CD4 gated, CD25$^+$FOXP3$^+$%) detected by flow cytometry for the naive CD4 T cells treated with the addition of antibodies G1 and G2 respectively on the basis of Mock (TCR) and GDF15 stimulation; C and D are bar statistical plots of the proportion of Treg cells detected by flow cytometry for A and B, respectively;

FIG. 6 is the results of the anti-tumor function of the anti-GDF15 monoclonal antibodies as detected by a co-culture experiment; wherein A is a hepa1-6-OVA real-time survival plot determined by xCELLigence RTCA impedance assay (ACEA Biosciences); B is a statistical plot of the hepa1-6-OVA cell survival at 140 h;

FIG. 7 shows the results of anti-tumor effect of the anti-GDF15 monoclonal antibody detected by a MC38 mouse tumor-bearing model; wherein A is the tumor body result display of a MC38 mouse carcinoma in situ model; B is tumor weight analysis; C is the individual tumor growth curve of the G1 monoclonal antibody group; D is the individual tumor growth curve of the control group; E is the comparison result of the tumor growth curves between control group and G1 monoclonal antibody group;

FIG. 8 shows the tumor inhibitory effects of the anti-GDF15 monoclonal antibodies in a liver cancer carcinoma in situ mouse model; wherein A is the size of the tumor in the dissected liver after 28 days in the carcinoma in situ model; B is the imaging display of small animals in vivo; C is a comparison of tumor growth curves between the control group and the drug group, wherein $P<0.001$ as compared to the control group.

DESCRIPTION OF EMBODIMENTS

In order for those skilled in the art to better understand the aspects of the present application, the embodiments of the present application will now be clearly and fully described in conjunction with the drawings in embodiments of the present application, and it will be apparent that the described embodiments are only some, but not all, embodiments of the present application. Based on the embodiments in the present application, all other embodiments obtained by a person of ordinary skill in the art without inventive step shall fall within the scope of protection of the present application.

It shall be noted that the terms "comprising" and "having" and any variations thereof in the description and claims of the application are intended to cover non-exclusive inclusion. For example, a process, method, system, product or apparatus that comprises a list of steps or elements is not necessarily limited to those steps or elements expressly listed but may include other steps or elements not expressly listed or inherent to such process, method, product or apparatus.

According to the application, a commercial recombinant GDF15 protein (R&D, 9279-GD) is used as antigen to immunize Balb/c mice, hybridoma cell lines capable of stably secreting a high-specificity anti-GDF15 monoclonal antibody are screened, and ascites is prepared to obtain a high-specificity anti-GDF15 monoclonal antibody; the CDR sequences of the gene sequences and corresponding protein sequences are confirmed and tagged to support anti-GDF15 chimeric or humanized genetically engineered antibodies. The present application will now be described in detail in connection with methods of preparation of specific monoclonal antibodies, detection of antibody specificity and activity, sequence detection and uniqueness determination, which is an explanation rather than a limitation of the present application. The present application will be described in further detail below with reference to the drawings:

1. Preparation and Purification of Anti-GDF15 Neutralizing Monoclonal Antibodies 1.1 Mouse Antigen Immunization Balb/c mice were immunized with a commercial GDF15 recombinant protein (R&D, 9279-GD) as an antigen, and the antigen was mixed with a Freund's adjuvant in equal volumes and thoroughly milled to a water-in-oil chylous fluid. The immunization was carried out for three times. The amount of the antigen used in naive mice was 10-50 ug/mouse. After being fully emulsified with the Freund's adjuvant, the fluid was injected into the mice at multiple points, generally 0.8-1 mL/mouse, and 0.2-0.3 mL/injection point. The second immunization was four weeks after the initial immunization and the antigen was injected in the same dose, method and route as the initial immunization. The third immunization was performed three weeks after the second immunization, the antigen was injected at the same dose as the first without Freund's adjuvant, and the antigen was dissolved in normal saline for intraperitoneal injection. The titers were measured 7-10 days later by blood sampling. After an interval of 2-3 weeks, the antigen was injected intraperitoneally to strengthen immunity, and the animals were sacrificed 3 days later and the spleen cells were taken for cell fusion.

1.2 Cell Fusion and Culture of Hybridomas $5$-$6\times10^7$ mouse myeloma cells (SP2/0) which were in the logarithmic growth phase with good growth were taken, and myeloma cells and spleen cells were fused in a ratio of 1:10 at room temperature: 1 ml of 50% PEG 4000 preheated at 37° C. was added in 30 s while stirring; the cells were sucked into a straw for 90 s; a preheated 37° C. incomplete medium was added at a constant speed to stop the PEG action, and 1 ml, 2 ml, 3 ml, 4 ml, 5 ml and 10 ml were continuously added and centrifuged at 800 rpm for 2 min. The fused cell suspension was added into a culture system containing feeder cells (peritoneal macrophages of normal Balb/c mice), and a HAT selective medium was used to adjust the serum concentration to 10%-20%; a $NaHCO_3$—$Na_2CO_3$ buffer system and HEPES were added and cultured in a 5%-10% $CO_2$ incubator at 37° C.

1.3 Screening of Positive Hybridomas

After clones emerged, positive clones were selected by indirect enzyme-linked immunosorbent assay (ELISA). Cells containing positive clonal wells were cloned by limiting dilution until hybridoma cell lines capable of stably secreting antibodies were obtained. The criteria for establishing the hybridoma cell lines were as follows: (1) 100% positive for four consecutive clonings; (2) stable antibody secretion capacity after in vitro serial passages for 3 months.

1.4 Ascites Generation and Ascites Titer Determination

Preparation of ascites: 0.5 ml Pristane was intraperitoneally injected into Balb/c mice to activate peritoneal macrophages of the mice to produce cytokines such as IL-6. One week later, $5\times10^5$ hybridoma cells were injected intraperitoneally and ascites fluid could be produced 7-10 days after inoculation. One week after the hybridoma cells were injected in this experiment, the mice were dying, so they were killed to absorb ascites as much as possible.

Ascites titer assay: titer assay was performed on ascites before purification using enzyme-linked immunosorbent assay (ELISA). The envelope antigen was GDF15 commercial recombinant protein at a concentration of 1 ug/ml-10 ug/ml, and the samples to be tested were serially diluted ascites and purified monoclonal antibodies. The measurement results of the ascites titers of the high-affinity monoclonal antibodies that have been screened out were as shown in FIG. 1. The ascites titer of the hybridoma corresponding to the anti-GDF15 neutralizing monoclonal antibody G1 (hereinafter referred to as the antibody G1) could reach $10^{-7}$, and that of the hybridoma corresponding to the anti-GDF15 neutralizing monoclonal antibody G2 (hereinafter referred to as the antibody G2) could reach $10^{-6}$. Generally, the antibody with an ascites titer above $1\times10^{-5}$ as determined by indirect ELISA can be used, so the two monoclonal antibodies screened out are available antibodies with high titers.

1.5 Purification of Antibodies

The ammonium sulfate salting-out method was used. After precipitation with 40% saturated ammonium sulfate, a dialysis bag (molecular cutoff: 10000 KD) was used for dialysis at 4 C overnight. Then, an AKTA FPLC chromatographic purification system was used, and a protein A+G Agarose (P2019-10 ml) chromatographic column was used for affinity purification of the monoclonal antibody, and the purification effect was analyzed by SDS-PAGE. The ascites purification results are shown in FIG. 2. Using the anti-GDF15 neutralizing monoclonal antibody G1 as an example, A is the affinity chromatography result of an AKTA FPLC chromatography purification system, with the first peak being the unbound sample loaded and the second peak being the sample after elution by a PH2.7 glycine eluent; B is an SDS-PAGE profile, I is a sample before affinity chromatography, and II is a sample after affinity chromatography. This result shows that after affinity chromatography, monoclonal antibodies with high purity were obtained.

2. Identification of Anti-GDF15 Monoclonal Antibodies 2.1 Monoclonal Antibody Sequencing to Obtain Antibody Subtypes and Sequences After antibody-producing hybridoma cells were grown to a certain scale (cell number>$3 \times 10^6$), the cells were lysed with Trizol. Total RNA from hybridoma cell lysate was extracted using Quick-RNA MicroPrep Kit, and RNA was isolated by agarose gel electrophoresis. 5 'RACE was performed by ClontechSMARTer RACE 5'/3'kit to obtain cDNA, which was used as a template for PCR amplification with PrimeSTAR® Max DNA Polymerase. The V region cDNA of the antibody was extracted, which was then sequenced by sequencing company. The subtype of the antibody G1 was IgG1, and the subtype of the antibody G2 was IgM, as known by sequencing. The amino acid sequence of the variable region and the corresponding base sequence of the antibody were obtained respectively, and meanwhile the CDR regions of the amino acid sequence and the corresponding base sequence of the antibody were marked by the Kabat method.

2.3 Affinity and Titer Determination of Monoclonal Antibodies

The binding of the GDF15 monoclonal antibodies to GDF15 molecules was determined by using surface plasmon resonance (SPR). The commercial GDF15 recombinant protein (R&D, 9279-GD) was used as a stationary phase, and the screened antibody was used as a mobile phase. Samples were loaded at gradient concentrations, and the interaction thereof were detected by SPR instrument. The results were analyzed by TraceDrawer (Ridgeview Instruments ab, Sweden) software using a One To One model, as shown in FIG. 3A and FIG. 3B. As can be seen from the concentration gradient binding curves and affinity parameters (KD) in the figure, the two GDF15 monoclonal antibodies that have been screened out have strong binding to GDF15, with an affinity of up to $7.14 \times 10^{-8}$ for the antibody G1 and $5.72 \times 10^{-7}$ for the antibody G2, all meeting the antibody usage criteria.

Figure 4:
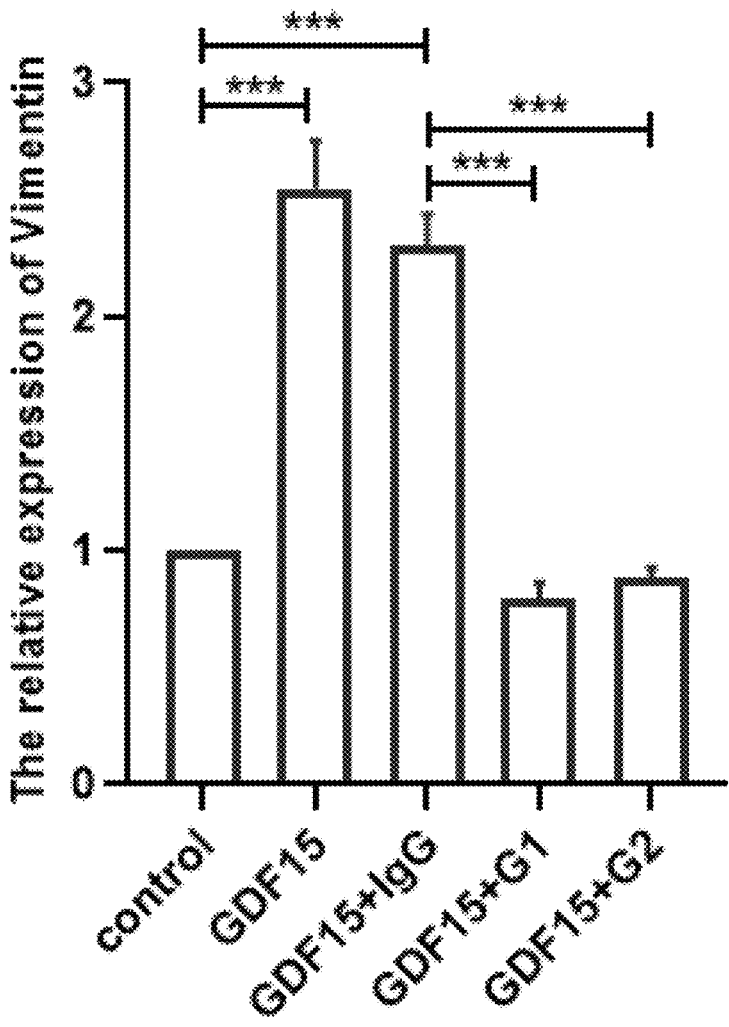
FIG. 4 shows the results of the neutralizing activity of the anti-GDF15 monoclonal antibodies G1 and G2 as detected by a Real-time PCR experiment.

3. Identification of Neutralization of Anti-GDF15 Monoclonal Antibody 3.1 Real-Time PCR Method to Verify Neutralizing Function of Monoclonal Antibodies Based on previous studies, GDF15 can significantly upregulate the mRNA level of VIM genes in Hepa1-6 cells, thus constructing a Real-time PCR validation system for GDF15 neutralizing antibodies. The screened antibodies (1 ug/ml) were added to this system, and it was found that both antibody G1 and antibody G2 were able to significantly inhibit the mRNA expression level of the VIM up-regulated by GDF15, as shown in FIG. 4, which demonstrates that both antibodies that have been screened out have the effect of neutralizing the biological activity of GDF15.

3.2 Translation of Variable Region Genes into Amino Acid Sequences for Amino Acid Sequence Analysis On the basis of previous studies, GDF15 was able to induce up-regulation of Foxp3 protein levels of naïve CD4+ T cells, thereby inducing differentiation of naïve CD4+ T cells towards regulatory T cells (Treg cells), thus constructing a flow cytometry validation system of GDF15-neutralizing antibodies. The screened antibody was added to a culture system of naïve CD4+ T cells induced by GDF15, and the expression level of Foxp3 was measured by flow cytometry. The result showed that the biological function of GDF15 for up-regulating Foxp3 expression was inhibited upon addition of the antibody and that this inhibition was shown to be dose dependent with the increase of the concentration of the antibody, as shown in FIG. 5, which demonstrates that both antibody G1 and antibody G2 that had been screened out have the effect of neutralizing the biological activity of GDF15.

4. Efficacy Validation of GDF15 Neutralizing Monoclonal Antibody 4.1 Co-culture System to Evaluate Inhibitory Effect of GDF15 Neutralizing Monoclonal Antibodies on Tumor Cell Growth On the basis of previous studies, GDF15 was able to induce differentiation of naïve CD4+ T cells into Treg cells, and Treg cells were able to suppress the killing activity of T cells against tumor cells. To evaluate whether GDF15 neutralizing monoclonal antibodies were able to block the immunomodulatory function of GDF15 and thereby promote killing of tumor cells by T cells, a co-culture system of T cells and tumor cells was constructed as follows:

1) Hepa1-6-OVA cells: pCI-neo-mOVA (Addgene plasmid #25099) plasmid was transfected into Hepa1-6 tumor cells with a lipo3000 transfection reagent (Invitrogen), pressure screening was performed using 400 ug/ml G418 (diyibio), finally obtaining stably expressing Hepa1-6-OVA cells.

2) OT-1 CD8 T cells: Splenic T cells were isolated from spleens of OT-I TCR transgenic mice and OT-1 CD8 T cells were obtained by sorting with CD8a (Ly-2) MicroBeads (MiltenyiBiotec) magnetic beads and stimulated with 10 nmol ml$^{-1}$ OVA$_{257\text{-}264}$ peptide (MCE) and 100 u/ml IL-2 for 72 h.

3) Naive CD4+ T cells: Splenic T cells were isolated from C57BL/6 mice and Naive CD4+ T cells were obtained by sorting with Naive CD4+ T Cell Isolation Kit (MiltenyiBiotec) magnetic beads. A GDF15 neutralizing monoclonal antibody was added on the basis of GDF15 and TCR (5 µg ml$^{-1}$ enveloped anti-CD3, 2 µg ml$^{-1}$ anti-CD28 and 100 u/ml IL-2) stimulation to detect its blocking effect. Since sequencing of the variable regions of the antibodies showed that the G1 antibody was IgG1, the G2 antibody was IgM, and IgG in general has a higher affinity and is suitable for later humanization, the G1 antibody was selected as the validation antibody used in this step.

The hepa1-6-OVA cells were inoculated on a 96-well plate at $1 \times 104$/well and the cells were counted at an interval of 1 hour by xCELLigence RTCA impedance measurement (ACEA Biosciences). The real-time survival of the Hepa1-6-OVA cells was monitored in real time. After 30 h of culture, pre-stimulated OT-1C8+ T and Naive CD4+ T were added to the well plate of hepa1-6-OVA according to the ratio of 2:1:2, and the cell survival was continuously monitored for 110 h. The cell count at each time point was normalized by the cell count at 29 h, and the Normalized cell index was obtained to analyze the cell survival.

As shown in FIG. 6, the killing function of OT-1C8+ T was inhibited in the GDF15 group, and more hepa1-6-OVA cells survived. After the antibody G1 was added, the ability of GDF15 for inducing naive CD4+ T into Treg was blocked, and hepa1-6-OVA cells were killed by OT-1C8+ T, and survived cells decreased. The results verified that the GDF15 neutralizing monoclonal antibody G1 could neutralize GDF15, block its differentiation effect on Treg cells, and promote the killing of tumor cells by killer T cells.

4.2 Measurement of Anti-Tumor Effect of GDF15 Neutralizing Monoclonal Antibody in MC38 Mouse Tumor Bearing Model Ten male C57 mice of 6-8 weeks were selected to construct a transplanted tumor model. The MC38 cells in good culture condition were prepared into a single cell suspension, which was mixed with a precooled DMEM medium and Matrigel at equal volumes of 1:1 to resuspend the cells to $1\times10^7$\ml (this process should be operated at low temperature to avoid the solidification of Matrigel). 0.5 ml of the MC38 cell suspension was subcutaneously injected into the back of each C57 mouse. Ten days later, after the subcutaneous tumor was obviously formed, the mice were given ear tags and the tumor volume was measured. According to the tumor volume, they were randomly divided into two groups, five in each group. The formula for calculating the tumor volume is $V=L\times S^2\times0.5$, where L is the longitudinal diameter of the tumor and S is the transverse diameter. From the 10th day, the tumor volume was measured every 5 days, and the drug was administered intraperitoneally. The control group was injected intraperitoneally with 125 ug IgG, and the monoclonal antibody group was injected intraperitoneally with 125 ug G1. The drugs were diluted with 100 ul normal saline for both groups. After four measurements, the mice were killed, the tumor was dissected and the tumor weight was measured. See FIG. 7 for the experimental results. It is found that the growth curve of the monoclonal antibody group was slower relative to the control group (FIGS. C, D, E), illustrating that the G1 monoclonal antibody used had a pronounced anti-tumor effect. After four times of administration, the tumor volume of the treatment group was significantly smaller than that of the control group (A and B in the figure), and the tumor weight of the treatment group (0.94±0.48 g) was also significantly smaller than that of the control group (1.82±0.56 g), with a tumor inhibition rate of 50.62%. The anti-tumor rates of the control group and monoclonal antibody group in the MC38 mouse tumor-bearing model are shown in Table 1 below. The experimental results show that the G1 antibody has the effect of inhibiting tumor growth.

TABLE 1

| Group | Dosage | Tumor Weight (g) | Tumor inhibition (%) |
| --- | --- | --- | --- |
| Control(IgG) | 100 μl(125μ) | 1.82 ± 0.56 | — |
| G15A | 100 μl(125μ) | 0.94 ± 0.48** | 50.62% |

P < 0.01 (n = 5, $\bar{\chi}$ ± s) compared to Control group 4.3 Anti-Tumor Effect of GDF15 Neutralizing Monoclonal Antibody in Hepatocellular Carcinoma In Situ Mouse Model Sixteen male C57 mice aged 6-8 weeks were selected to construct a model of hepatocellular carcinoma in situ. Before inoculating the tumor, the hair was removed from the abdomen to be inoculated below the xiphoid process of mice in advance, and hepa1-6-luc cells were prepared into a single cell suspension, and the same volume of Matrigel gel was added to resuspend for later use. After the mice were anesthetized with phenobarbital sodium, the abdomen was opened 1-2 cm below the xiphoid process, and the liver was carefully squeezed out. Each mouse was injected with $3\times10^6$ cells, with an injection volume of about 50 ul. The injection was carried out slowly to prevent leakage. After the injection, the peritoneum and epidermis were sutured respectively, and ear tags were attached. On the third day after operation, small animal in vivo imaging was carried out, and the tumors of hepatocellular carcinoma in situ were randomly divided into groups by stratification based on sizes according to the imaging results. They were divided into two groups: an administration group and a control group. After grouping, small animal in vivo imaging was carried out on 7th, 14th and 21st day after operation, and the imaging results were collected and analyzed. Intraperitoneal administration was started on the 5th day after operation, and administration was carried out three times on the 5th, 12th and 19th days. The control group was intraperitoneally injected with 100 ul saline (containing 125 ug IgG), and the monoclonal antibody group was intraperitoneally injected with 125 ug G1 antibody diluted with 100 ul saline. After 28 days, the mice were killed and the liver tumors were dissected to observe the sizes. See FIG. 8** for the results The results show that compared with the control group, the growth of the tumor in the monoclonal antibody group was obviously inhibited after treatment with the G1 monoclonal antibody (FIG. C), and the tumor volume in the administration group was significantly smaller than that in the control group (FIGS. A and B). The results showed that the G1 monoclonal antibody had a good anti-tumor effect in the hepatocellular carcinoma in situ model.

To sum up, in the present application, anti-GDF15 mouse monoclonal antibodies were prepared by the hybridoma technology, anti-GDF15 hybridoma cell lines capable of stable secretion with high specificity were screened out, ascites were prepared to obtain high-specificity and high-affinity anti-GDF15 monoclonal antibodies and two anti-GDF15 monoclonal antibodies with neutralizing activity were identified for the first time by constructing a simple and stable antibody neutralization detection system. Based on the study of immune regulation of GDF15, the inhibitory effect of the neutralizing monoclonal antibodies on tumor growth was verified in vitro and in vivo by establishing a co-culture system of lymphocytes and tumor cells and the tumor-bearing experiment in mice, which laid a foundation for humanization of antibodies and the use thereof in tumor immunotherapy and metabolism related diseases.

The above contents only illustrate the technical idea of the present invention, and are not intended to limit the protection scope of the present application. Any changes made on the basis of the technical solution according to the technical idea put forward by the present application shall fall within the protection scope of the claims of the present application.

What is claimed is:

1. An anti-GDF15 neutralizing monoclonal antibody G1 comprising a light chain and a heavy chain, wherein, three complementarity determining region sequences of a variable region of the light chain are respectively:

```
CDR1:
        (amino acids 24-34 of SEQ ID NO: 1)
Arg-Ala-Ser-Glu-Asn-Ile-Tyr-Ser-Asn-Leu-Ala;

CDR2:
        (amino acids 50-56 of SEQ ID NO: 1)
Val-Ala-Thr-Asn-Leu-Val-Asp;

CDR3:
        (amino acids 89-97 of SEQ ID NO: 1)
Gln-His-Phe-Trp-Gly-Thr-Pro-Trp-Thr;
``` three complementarity determining region sequences of a variable region of the heavy chain are respectively:

```
CDR1:
        (amino acids 31-36 of SEQ ID NO: 2)
Ser-Ala-Tyr-Ala-Trp-Asn;

CDR2:
        (amino acids 50-66 of SEQ ID NO: 2)
Tyr-Ile-Ser-Tyr-Ser-Gly-Ser-Thr-Ser-Tyr-Asn-Pro-
Ser-Leu-Lys-Ser;
```

-continued

```
CDR3:
        (amino acids 99-105 of SEQ ID NO: 2)
Gly-Gly-Asp-Ala-Glu-Asp-Tyr.
```

2. The anti-GDF15 neutralizing monoclonal antibody G1 according to claim 1, wherein in the monoclonal antibody G1, the amino acid sequence of the variable region of the light chain is as shown in SEQ.ID.NO. 1, and the amino acid sequence of the variable region of the heavy chain of the monoclonal antibody G1 is as shown in SEQ.ID.NO. 2.

3. The anti-GDF15 neutralizing monoclonal antibody G1 according to claim 1, wherein the nucleotide sequence encoding the variable region of the light chain is as shown in SEQ.ID.NO.5, and the nucleotide sequence encoding the variable region of the heavy chain is as shown in SEQ.ID.NO.6.

4. A method for anti-tumor or tumor immunotherapy, wherein the method comprises: administrating the anti-GDF15 neutralizing monoclonal antibody G1 of claim 1 to tumor cells of a subject in need thereof, wherein said subject is a colon carcinoma or hepatocellular carcinoma patient.

5. A method for treating metabolic disease, wherein the method comprises: administrating the anti-GDF15 neutralizing monoclonal antibody G1 of claim 1 to a subject in need thereof, wherein said subject is an anorexia or cachexia patient.

* * * * *

SEQUENCE LISTING

Sequence total quantity: 8
SEQ ID NO: 1              moltype = AA   length = 107
FEATURE                   Location/Qualifiers
source                    1..107
                          mol_type = protein
                          organism = synthetic construct
SEQUENCE: 1
DIQMTQSPAS LSVSVGETVT ITCRASENIY SNLAWFQQKQ GKSPQLLVYV ATNLVDGVPS   60
RFSGSGSGTQ YSLKINSLQS EDFGTYYCQH FWGTPWTFGG GTKLEIK             107

SEQ ID NO: 2              moltype = AA   length = 116
FEATURE                   Location/Qualifiers
source                    1..116
                          mol_type = protein
                          organism = synthetic construct
SEQUENCE: 2
DVQLQESGPG LVKPSQSLSL TCTVTGYSIT SAYAWNWIRQ FPGNKLEWMG YISYSGSTSY   60
NPSLKSRISI TRDTSKNQFF LQFNSVTTED TATYYCARGG DAEDYWGQGT TLTVSS     116

SEQ ID NO: 3              moltype = AA   length = 107
FEATURE                   Location/Qualifiers
source                    1..107
                          mol_type = protein
                          organism = synthetic construct
SEQUENCE: 3
QIVLSQSPAI LSASPGEKVT MTCRASSSVS YMHWYQQKPG SSPKPWIYAT SNLASGVPAR   60
FSGSGSGTSY SLTISRVEAE DAATYYCQQW SSNPPFTFGS GTKLEIK             107

SEQ ID NO: 4              moltype = AA   length = 121
FEATURE                   Location/Qualifiers
source                    1..121
                          mol_type = protein
                          organism = synthetic construct
SEQUENCE: 4
QVQLQQSGAE LARPGASVKL SCKASGYTFT DYYINWVKQR TGQGLEWIGE IYPGSGNTYY   60
NEKFKGKATL TADKSSSTAY MQLSSLTSED SAVYFCARVR ALLRPLAMDY WGQGTSVTVS  120
S                                                               121

SEQ ID NO: 5              moltype = DNA   length = 321
FEATURE                   Location/Qualifiers
source                    1..321
                          mol_type = other DNA
                          organism = synthetic construct
SEQUENCE: 5
gacatccaga tgactcagtc tccagcctcc ctatctgtat ctgtgggaga aactgtcacc   60
atcacatgtc gagcaagtga aaatatttac agtaatttag catggtttca gcagaaacag  120
ggaaaatctc ctcagctcct agtctatgtt gcaacaaact tagtagatgg tgtgccatca  180
aggttcagtg gcagtggatc aggcacacag tattccctca agatcaacag cctgcagtct  240
gaagattttg ggacttatta ttgtcaacat ttttgggta ctccgtggac gttcggtgga   300
ggcaccaagc tggaaatcaa a                                          321

SEQ ID NO: 6              moltype = DNA   length = 348
FEATURE                   Location/Qualifiers
source                    1..348
                          mol_type = other DNA
                          organism = synthetic construct
SEQUENCE: 6
gatgtgcagc ttcaggagtc gggacctggc ctggtgaaac cttctcagtc tctgtccctc   60
acctgcactg tcacaggcta ctcaatcacc agtgcttatg cctggaactg gatccggcag  120
tttccaggaa acaaactgga gtggatgggc tacataagct acagtggtag cactagctac  180
aacccatctc tcaaaagtcg aatctctatc actcgagaca catccaagaa ccagttcttc  240
ctgcagttca attctgtgac tactgaggac acagccacat attactgtgc aagagggggg  300
gacgcagagg actactgggg ccaaggcacc actctcacag tctcctca             348

SEQ ID NO: 7              moltype = DNA   length = 321
FEATURE                   Location/Qualifiers
source                    1..321
                          mol_type = other DNA
                          organism = synthetic construct
SEQUENCE: 7
caaattgttc tctcccagtc tccagcaatc ctgtctgctt ctccagggga gaaggtcaca   60
atgacttgca gggccagctc aagtgttagt tacatgcact ggtaccagca gaagccagga  120
tcctccccca aaccctggat ttatgccaca tccaacctgg cttctggagt ccctgctcgc  180
ttcagtggca gtgggtctgg gacctcttac tctctcacaa tcagcagagt ggaggctgaa  240
gatgctgcca cttattactg ccagcagtgg agtagtaacc caccattcac gttcggctcg  300
gggacaaagt tggaaataaa a                                          321

SEQ ID NO: 8              moltype = DNA   length = 363

-continued

```
FEATURE              Location/Qualifiers
source               1..363
                     mol_type = other DNA
                     organism = synthetic construct
SEQUENCE: 8
caggttcagc tgcagcagtc tggagctgag ctggcgaggc ccggggcttc agtgaagctg  60
tcctgcaagg cttctggcta caccttcact gactactata taaactgggt gaagcagagg  120
actggacagg gccttgagtg gattggagag atttatcctg gaagtggtaa tacttactac  180
aatgagaagt tcaagggcaa ggccacactg actgcagaca aatcctccag cacagcctac  240
atgcagctca gcagcctgac atctgaggac tctgcagtct atttctgtgc aagagtgagg  300
gcattactac ggcctctcgc tatggattat tggggtcaag gaacctcagt caccgtctcc  360
tca                                                             363
```